United States Patent [19]

Patterson et al.

[11] Patent Number: 5,001,124
[45] Date of Patent: Mar. 19, 1991

[54] 4-ISOXAZOLECARBOXAMIDE DERIVATIVES

[75] Inventors: John W. Patterson, Mountain view; Bruce H. Devens, Palo Alto, both of Calif.

[73] Assignee: Syntex (U.S.A.) Inc., Palo Alto, Calif.

[21] Appl. No.: 474,430

[22] Filed: Feb. 2, 1990

[51] Int. Cl.$^5$ .................. A61K 31/535; A61K 31/42; C07D 413/42; C07D 413/14

[52] U.S. Cl. .................. 514/236.8; 514/378; 544/140; 544/165; 546/233; 548/248; 548/568; 549/68; 549/72; 549/480; 549/487; 564/200

[58] Field of Search .................. 544/140; 548/248; 514/236.8, 378

[56] References Cited

U.S. PATENT DOCUMENTS

| | | | |
|---|---|---|---|
| 4,087,535 | 5/1978 | Heubach et al. | 514/378 |
| 4,284,786 | 8/1981 | Kämmerer et al. | 548/248 |
| 4,351,841 | 9/1982 | Kämmerer et al. | 514/378 |
| 4,935,434 | 6/1990 | Han | 514/378 |

FOREIGN PATENT DOCUMENTS

| | | |
|---|---|---|
| 0257882 | 3/1988 | European Pat. Off. |
| 0259972 | 3/1988 | European Pat. Off. |
| 3247454 | 6/1984 | Fed. Rep. of Germany |
| 3534440 | 4/1987 | Fed. Rep. of Germany |

OTHER PUBLICATIONS

Sato et al., Chem. Pharm. Bull., 31, p. 1896, (1983).

Primary Examiner—Mukund J. Shah
Assistant Examiner—F. Bernhardt
Attorney, Agent, or Firm—Carol J. Roth; Derek P. Freyberg; Tom M. Moran

[57] ABSTRACT

This invention is directed to compounds of the formula (I):

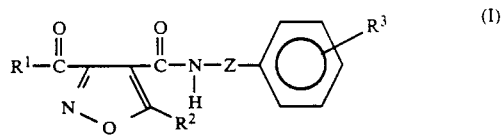

wherein
$R^1$ is —OR$^4$ (where R$^4$ is hydrogen, lower alkyl, lower hydroxyalkyl, phenyl, phenyl-lower-alkyl, or —(CH$_2$)$_n$Y where n is an integer from 1 to 4 and Y is morpholino, -SR$^5$, —C(O)OR$^5$, —C(O)N(R$^6$)$_2$, —N(R$^6$)$_2$, or —N$^+$(R$^6$)$_3$X$^-$, in which R$^5$ is lower alkyl, each R$^6$ is independently selected from hydrogen or lower alkyl, and X is halogen) or —SR$^7$ (where R$^7$ is lower alkyl, phenyl-lower-alkyl, or —(CH$_2$)$_n$W where W is —N(R$^6$)$_2$ or —N$^+$(R$^6$)$_3$X$^-$, and n, R$^6$ and X are as previously defined);
$R^2$ is lower alkyl, phenyl or phenyl-lower-alkyl;
$R^3$ is halo, hydroxy, lower alkyl, lower alkoxy, lower haloalkyl, lower haloalkoxy, or —C(O)OR$^5$ where R$^5$ is as previously defined; and
Z is a bond, 2,5-thienyl or 2,5-furanyl; or a pharmaceutically acceptable salt thereof. These compounds are useful in treating inflammation, autoimmune disease or allograft rejection in mammals.

16 Claims, No Drawings

4-ISOXAZOLECARBOXAMIDE DERIVATIVES

BACKGROUND OF THE INVENTION

1. Field of the Invention

This invention relates to 4-isoxazolecarboxamide derivatives and their pharmaceutically acceptable salts, particularly those derivatives which are substituted at the 3-position by a carboxylic acid group or ester and at the 5-position by a lower alkyl group. These compounds are useful in treating inflammation, autoimmune disease, allograft rejection or graft-versus-host rejection in mammals. This invention also relates to pharmaceutical compositions containing such compounds.

2. Related Disclosures

U.S. Pat. No. 4,284,786 (Hoechst AG) discloses the compound of the formula:

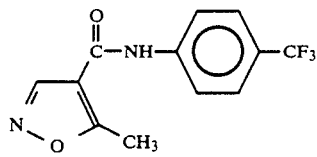

namely, 5-methyl-N-(4-trifluoromethylphenyl)-4-isoxazolecarboxamide, also known as HWA-486, which is disclosed as being useful as an antirheumatic, antiphlogistic, antipyretic and analgesic agent, and for the treatment of multiple sclerosis. U.S. Pat. No. 4,351,841 discloses a method of using HWA-486 in the treatment of inflammation, rheumatism or multiple sclerosis, and West German Offenlegungsschrift 35 34 440 (Hoechst AG) discloses using HWA 486 in the treatment of graft versus host diseases and autoimmune diseases.

U.S. Pat. No. 4,087,535 (Hoechst AG) discloses compounds of the formula:

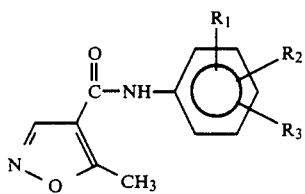

wherein each of $R^1$, $R^2$ and $R^3$ can be hydrogen, halo, or optionally substituted lower alkoxy or lower alkyl. These compounds are disclosed as being useful as anti-inflammatory and analgesic agents.

European Published Patent Application No. 0 259 972 (Lilly) discloses compounds of the formula:

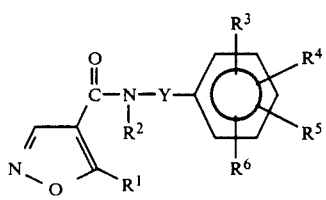

wherein each of $R^1$ and $R^2$ can be hydrogen or lower alkyl: each of $R^3$, $R^4$, $R^5$ and $R^6$ can be hydrogen, hydroxy, halogen, nitro, cyano, lower alkyl, lower alkoxy, lower haloalkyl, lower haloalkoxy; and Y is a 5-or 6-membered heterocyclic ring excluding pyrazole. These compounds are disclosed as being useful in treating immune diseases such as arthritis and for treating diseases in which leukotrienes are implicated.

The disclosures of these and all other documents referred to in this specification are incorPorated herein in whole by reference.

SUMMARY OF THE INVENTION

In a first aspect, this invention provides a group of compounds represented by formula (I):

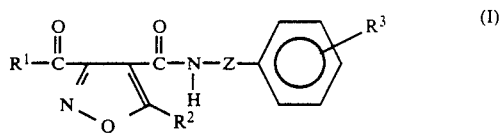

wherein $R^1$ is -$OR^4$ (where $R^4$ is hydrogen, lower alkyl, lower hydroxyalkyl, phenyl, phenyl-lower-alkyl, or -$(CH_2)_nY$ where n is an integer from 1 to 4 and Y is morpholino, -$SR^5$, -$C(O)OR^5$, -$C(O)N(R^6)_2$, -$N(R^6)_2$, or -$N^+(R^6)_3X^-$, in which $R^5$ is lower alkyl, each $R^6$ is independently selected from hydrogen or lower alkyl, and X is halogen)

or -$SR^7$ (where $R^7$ is lower alkyl, phenyl-lower-alkyl, or -$(CH_2)_nW$ where W is -$N(R^6)_2$ or -$N^+(R^6)_3X^-$, and n, $R^6$ and X are as previously defined);

$R^2$ is lower alkyl, phenyl or phenyl-lower-alkyl;

$R^3$ is halo, hydroxy, lower alkyl, lower alkoxy, lower haloalkyl, lower haloalkoxy, or -$C(O)OR^5$ where $R^5$ is as previously defined; and Z is a bond. 2,5-thienyl or 2,5-furanyl; or a pharmaceutically acceptable salt thereof.

In another aspect, this invention provides compositions useful in the treatment of inflammation, autoimmune disease, allograft rejection and graft-versus-host rejection in mammals, wherein the composition comprises a therapeutically effective amount of a compound of formula (I) as described above and a pharmaceutically acceptable excipient.

In another aspect, this invention provides a method for treating an autoimmune disease in a mammal wherein the method comprises administering to the mammal in need thereof a therapeutically effective amount of a compound of formula (I).

In another aspect, this invention provides a method for treating allograft rejection in a mammal, which comprises administering to a mammal in need thereof a therapeutically effective amount of a compound of formula (I).

In another aspect, this invention provides a method for treating inflammation in a mammal, which comprises administering to the mammal in need thereof a therapeutically effective amount of a compound of formula (I).

In another aspect, this invention provides a method for treating graft-versus-host rejection in a mammal, which comprises administering to the mammal in need thereof an therapeutically effective amount of a compound of formula (I).

In another aspect, this invention provides a process for preparing compounds of formula (I).

DETAILED DESCRIPTION OF THE INVENTION

Definitions

As used in the specification and appended claims, unless specified to the contrary, the following terms have the meaning indicated:

The term "lower alkyl" refers to a straight or branched chain monovalent radical consisting solely of carbon and hydrogen, containing no unsaturation and having from one to four carbon atoms, e.g., methyl, ethyl, n-propyl, 1-methylethyl, n-butyl, 1-methylpropyl, and 1,1-dimethylethyl.

The term "lower hydroxyalkyl" refers to a lower alkyl radical as defined above that is substituted by one or more hydroxy groups, e.g., hydroxymethyl, 2-hydroxyethyl, 2,4-dihydroxybutyl, and the like.

The term "lower haloalkyl" refers to a lower alkyl radical as defined above that is substituted by one or more halogen atoms, e.g., trifluoromethyl, difluoromethyl, trichloroethyl, and the like.

The term "lower alkoxy" refers to a radical of the form $-OR_a$, where $R_a$ is lower alkyl as defined above, e.g., methoxy, ethoxy, n-propoxy, 1-methylethoxy, n-butoxy, 1,1-dimethylethoxy, and the like.

The term "lower haloalkoxy" refers to a lower alkoxy radical as defined above that is substituted by one or more halogen atoms, e.g., trifluoromethoxy, difluoromethoxy, trichloroethoxy, and the like.

The term "phenyl" refers to the benzene radical, i.e., $C_6H_5$.

The term "phenyl-lower-alkyl" refers to a lower alkyl radical as defined above that is substituted by a phenyl group, as defined above, e g., benzyl, 2-phenylethyl, 1-phenylethyl, phenylpropyl, 2-phenylpropyl, and the like.

The term "pharmaceutically acceptable salt" refers to those salts which retain the biological effectiveness and properties of the free bases and which are not biologically or otherwise undesirable. These salts may be prepared from either inorganic or organic bases. Salts derived from inorganic bases include, but are not limited to, the sodium, potassium, lithium, ammonium, calcium, magnesium, ferrous, zinc, copper, manganous, aluminum, ferric, and manganic salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The term "mammal" includes humans and all domestic and wild mammals, including, without limitation, cattle, horses, swine, sheep, goats, dogs, cats, rabbits, and the like.

The term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis and type I diabetes.

The term "allograft rejection" refers to the humoral or cellular immune response mounted by the immune system of a mammal after it has received a histoincompatible tissue graft from another mammal of the same species, thereby producing tissue injury in such a mammal.

The term "graft-versus host rejection" refers to the immune response that originates from transplanted graft tissue, in particular, transPlanted bone-marrow tissue, and that is directed towards the host tissue, thereby producing tissue injury in the host.

The terms "treatment" or "treating" as used herein cover any treatment of one or more of the conditions of inflammation, autoimmune disease, allograft rejection or graft-versus-host rejection in a mammal and include:

(i) preventing the condition from occurring in a mammal, in particular, when such mammal is predisposed to the condition but has not yet been diagnosed as having it;

(ii) inhibiting the condition, i.e., arresting its development: or (iii) relieving the condition, i.e., causing regression of the condition.

The term "therapeutically effective amount" refers to that amount of a compound of formula (I) which, when administered to a mammal in need thereof, is sufficient to effect treatment, as defined above, for inflammation, autoimmune disease, allograft rejection or graft-versus host rejection. What amount constitutes a "therapeutically effective amount" will vary depending on the compound, the condition and its severity, and the mammal to be treated, but may be determined routinely by one of ordinary skill in the art having regard to his own knowledge and to this disclosure.

The nomenclature used herein is basically a modified form of I.U.P.A.C. nomenclature wherein compounds of formula (I) are named as derivatives of 4-isoxazolecarboxamide. The positions in the compounds are indicated as follows:

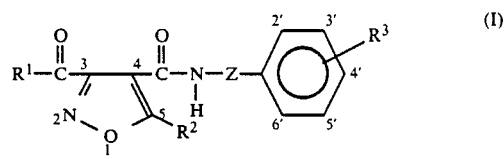

Thus, the following compound, a compound of formula (I) wherein $R^1$ is -OH, $R^2$ is methyl, $R^3$ is 4'-trifluoromethyl and Z is a bond, is named 3-carboxy-5-methyl-N-(4'-trifluoromethyl)phenyl-4-isoxazolecarboxamide:

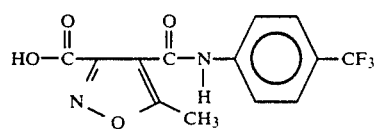

Utility and Administration

A. General Utility

The compounds of the invention, including the pharmaceutically acceptable salts thereof, and the compositions containing them, are useful as anti-inflammatory agents and as immunomodulatory agents In particular, these compounds are immunosuppressive, thereby decreasing the ability of animals to mount a cell-mediated or humoral immune response to certain antigens. The compounds are therefore useful in treating autoimmune diseases in mammals, such as systemic lupus erythematosus, type I diabetes and rheumatoid arthritis. In addition, because of their ability to suppress the immune response in animals, these compounds are useful in treating allograft rejection in mammals as a result of tissue transplantation. In addition, these compounds are useful in treating graft-versus host reJection in mammals. The compounds and compositions of the invention may be used prophylactically (e.g., to prevent allograft rejection) and/or therapeutically.

B. Testing

The immunomodulatory and anti-inflammatory activity of the compounds of the invention can be determined by a variety of assays. In particular, immunosuppressive activity can be determined by both in vivo and in vitro procedures.

In vivo procedures may utilize the Jerne hemolytic plaque assay, [Jerne, et al., "The agar plaque technique for recognizing antibody producing cells," Cell-bound Antibodies, Amos, B. and Kaprowski, H editors (Wistar Institute Press, Philadelphia) 1963, p. 109]or a modification thereof, or the cytolytic T cell assay as described in Brunner, et al., *Immunology* (1968), Vol. 14, p. 181, or a modification thereof, or the oxazolone-induced delayed-type hypersensitivity assay as described in Young, J., et al., *Pharmocological Methods in the Control of Inflammation*, 1989, p. 215-231, or a modification thereof.

In vitro procedures may utilize the cytolytic T-cell assay (CTL) as described in Wunderlich, et al , *Nature* (1970), Vol. 228, p. 62, or a modification thereof, or the Mishell-Dutton assay as described in Mishell, et al , *Journal of Experimental Medicine* (1967), Vol. 126, p. 423, or a modification thereof.

Autoimmune activity can be determined utilizing the experimental allergic encephalomyelitis assay as initially described by Grieg, et al., *J. Pharmacol. Exp. Ther.*, 1970, Vol. 173, page 85, or a modification thereof. Anti inflammatory activity may also be determined by the adjuvant arthritis assay according to the method of Winter, et al., *Arthritis and Rheumatism* (1966), Vol. 9, p. 394-403, or a modification thereof.

C. General Administration

Administration of the active compounds of formula (I), in pure form or in an appropriate pharmaceutical composition, can be carried out via any of the accepted modes of administration of agents for serving similar utilities. Thus, administration can be, for example, orally, nasally, parenterally or topically, in the form of solid, semi-solid, lyophilized powder, or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of formula (I) and, in addition, may include other medicinal agents, pharmaceutical agents, carriers, adjuvants, etc.

Generally, depending on the intended mode of administration, the pharmaceutically acceptable compositions will contain about 1% to about 99% by weight of the pharmaceutically active compound of this invention and 99% to 1% by weight of a suitable pharmaceutical excipient. Preferably, the composition will be about 5% to 75% by weight of a pharmaceutically active compound, with the rest being suitable pharmaceutical excipients.

The preferred manner of administration is oral using a convenient daily dosage regimen which can be adjusted according to the degree of affliction. For such oral administration, a pharmaceutically acceptable composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

The active compounds of formula (I) may be formulated into a suppository using, for example, about 0.5% to about 50% active ingredient disposed in a carrier that slowly dissolves within the body, e.g., polyoxyethylene glycols and polyethylene glycols (PEG) [e.g., PEG 1000 (96%) and PEG 4000 (4%)].

Liquid pharmaceutically administrable compositions can, for example, be prepared by dissolving, dispersing, etc. an active compound (about 0 5% to about 20%), as described above, and optional pharmaceutical adjuvants in a carrier, such as, for example, water, saline, aqueous dextrose, glycerol, ethanol and the like, to thereby form a solution or suspension.

If desired, the pharmaceutical composition to be administered may also contain minor amounts of auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see *Remington's Pharmaceutical Sciences*, 16th Ed., (Mack Publishing Company, Easton, Pa., 1980). The composition to be administered will, in any event, contain a therapeutically effective amount of the active compound for relief of the particular condition being treated when administered in accordance with the teachings of this invention.

Generally, the compounds of formula (I) are administered in a therapeutically effective amount which will vary depending on the individual and condition being treated. Typically, a therapeutically effective daily dose is from about 0.02 to 100 mg/kg of body weight per day of a compound of formula (I), for example, from about 0.4 to 30 mg/kg of body weight per day, and most preferably about 10 mg/kg/day. Thus, for administration to a 70 kg person, the dosage range would be from about 1.4 mg to 7.0 g per day, preferably from about 28

Preferred Embodiments

One aspect of the invention is the group of compounds represented by formula (I):

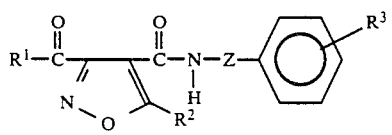

wherein $R^1$ is -$OR^4$ (where $R^4$ is hydrogen, lower alkyl, lower hydroxyalkyl, phenyl, phenyl-lower-alkyl, or -$(CH_2)_nY$ where n is an integer from 1 to 4 and Y is morpholino, -$SR^5$, -$C(O)OR^5$, -$C(O)N(R^6)_2$, -$N(R^6)_2$, or -$N^+(R^6)_3X^-$, in which $R^5$ is lower alkyl, each $R^6$ is independently selected from hydrogen or lower alkyl, and X is halogen)

or -$SR^7$ (where $R^7$ is lower alkyl, phenyl-lower-alkyl, or -$(CH_2)_nW$ where W is -$N(R^6)$ or -$N^+(R^6)_3X^-$, and n, $R^6$ and X are as previously defined);

$R^2$ is lower alkyl, phenyl or phenyl-lower-alkyl;

$R^3$ is halo, hydroxy, lower alkyl, lower alkoxy, lower haloalkyl, lower haloalkoxy, or -$C(O)OR^5$ where $R^5$ is as previously defined; and Z is a bond, 2.5-thienyl or 2,5-furanyl; or a pharmaceutically acceptable salt thereof. Within this group of compounds certain subgroups are preferred. These subgroups and their relative degrees of preference are described below.

A preferred subgroup of compounds is that subgroup wherein $R^1$ is -$OR^4$. Within this subgroup a preferred class of compounds is that class wherein $R^4$ is hydrogen, lower alkyl or -$(CH_2)_nY$. Within this class a preferred subclass of compounds is that subclass wherein $R^4$ is hydrogen.

Another preferred subgroup of compounds is that subgroup wherein $R^2$ is lower alkyl. Within this subgroup a preferred class of compounds is that class wherein $R^2$ is methyl.

Another preferred subgroup of compounds is that subgroup wherein $R^3$ is in the 4'-position and is lower alkyl, lower alkoxy, lower haloalkyl or lower haloalkoxy. Within this subgroup a preferred class of compounds is that class wherein $R^3$ is 4'-(1,1-dimethylethyl), 4'-methoxy, 4'-trifluoromethyl or 4'-trifluoromethoxy.

Another preferred subgroup of compounds is that subgroup where Z is a bond.

Preferred compounds of the invention are those where at least one of $R^1$, $R^2$ or $R^3$ is preferred as described above and Z is a bond. More preferred are those compounds where more than one of $R^1$, $R^2$ or $R^3$ is preferred as described above and Z is a bond. Even more preferred are those compounds where each of $R^1$, $R^2$ and $R^3$ is preferred as described above and Z is a bond. Presently, the most preferred compounds of this invention are:

3-carboxy-5-methyl-N-(4'-trifluoromethyl)phenyl 4-isoxazolecarboxamide; and 3-carboxy-5-methyl-N-(4'-trifluoromethoxy)phenyl-4-isoxazolecarboxamide.

Processes for Preparing Compounds of Formula (I)

A. Preparation of Compounds of Formula (Ia)

Compounds of formula (Ia) are compounds of formula (I) wherein $R^1$ is -$OR^4$ (where $R^4$ is lower alkyl), and $R^2$, $R^3$ and Z are as defined above in the Summary of the Invention They are synthesized as shown in the following Reaction Scheme 1 wherein $R^8$ is a bond, -$CH_2$- or -O-:

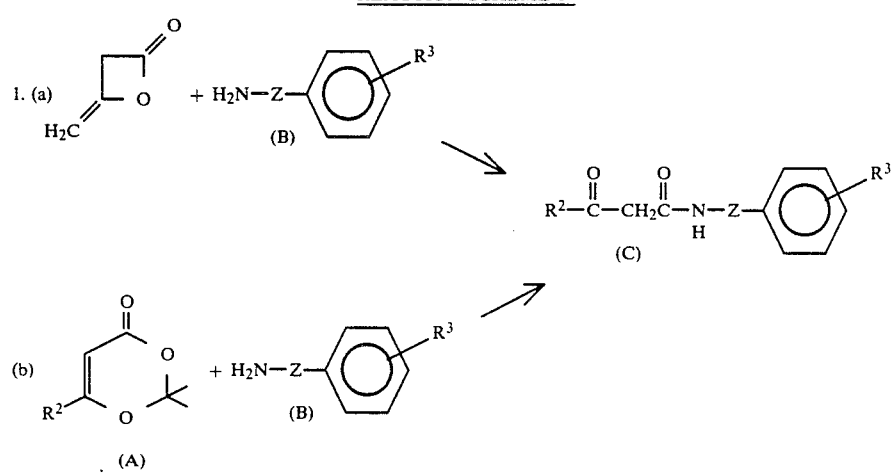

REACTION SCHEME 1

-continued
REACTION SCHEME 1

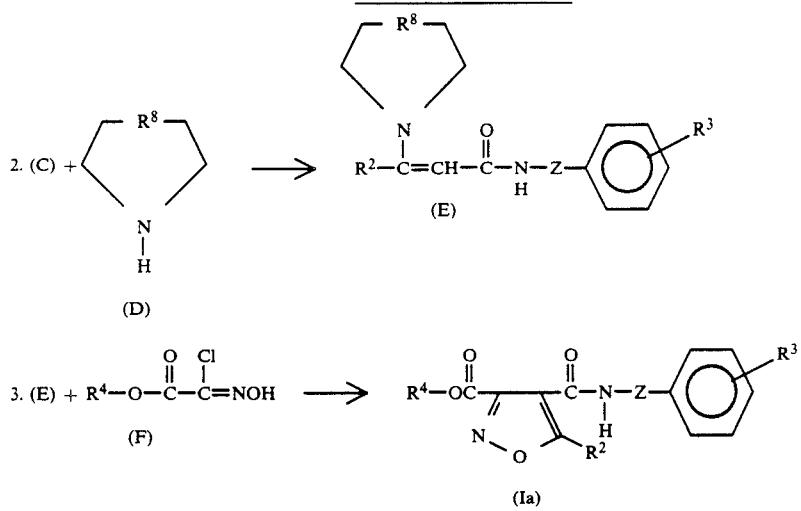

Dioxinones of formula (A) wherein $R^2$ is methyl are commercially available, for example, from Aldrich Chemical Co. Dioxinones of formula (A) wherein $R^2$ is lower alkyl, phenyl or phenyl-lower-alkyl may be prepared according to the methods described in *Chem. Pharm. Bull.*, 1984, Vol. 32, pages 102 and 3848, and *Chem. Pharm. Bull.*, 1983, Vol. 31 page 1896.

Diketene is commercially available, for example, from Aldrich Chemical Co.

Anilines of formula (B) are commercially available when Z is a bond for example, from the Aldrich Chemical Co. Anilines of formula (B) when Z is 2,5-thienyl or 2,5-furanyl may be prepared as in the following Reaction Scheme 2 or as in the method described in European Patent Application 0 259 972 (Lilly).

Cyclic secondary amines of formula (D), i.e., pyrrolidine, piperidine or morpholine, are commercially available, for example, from Aldrich Chemical Co.

Alkyl chlorooximidoacetates of formula (F) may be prepared according to the method described in *J. Orz. Chem.*, 1983, Vol. 48, No. 3, 366 372, or by methods known to those skilled in the art.

In general, the compounds of formula (Ia) are prepared by first either treating the aniline of formula (B) with at least equimolar amount of diketene (Step 1a) in a neutral solvent, preferably toluene, at temperatures between 20° C. and 100° C., preferably at about 55° C., for about 10 minutes to 6 hours, preferably for about 4 hours to form compounds of formula (C). Alternatively, compounds of formula (C) are prepared by treating the aniline of formula (B) with at least an equimolar amount of a dioxinone of formula (A) (Step 1b) in an aprotic solvent, for example, benzene or xylene, preferably xylene, and allowed to reflux at temperatures between 90° C. to 140° C., for about 10 minutes to 1 hour, preferably for about 35 minutes. Compounds of formula (C) are then converted into the compounds of formula (E) by reaction with a cyclic secondary amine of formula (D), in a neutral solvent, preferably benzene. The reaction mixture is then heated at temperatures from about 30° C. to about 120° C. for about 30 minutes to about 6 hours, preferably 1 hour, to form compounds of formula (E), which are isolated from the reaction mixture by standard isolation techniques. Compounds of formula (E) are then treated with an alkyl chlorooximidoacetate of formula (F) either in the presence of triethylamine, as described in the *J. Orz. Chem.* article, supra, or, in the absence of triethylamine, in methylene chloride or other neutral solvents, for example, diethyl ether or tetrahydrofuran, at about 0° C. to about 50° C., preferably at about 0° C. to about 10° C., for about 1 hour to 6 hours, preferably for about 2 to 4 hours, to form compounds of formula (Ia). If triethylamine is used, undesirable by-products are also prepared as a result of amination of the compounds of formula (Ia) by the cyclic secondary amine.

B. Preparation of Compounds of Formula (Ib)

The compounds of formula (Ib) are compounds of formula (I) wherein $R^1$ is -OH and $R^2$, $R^3$ and Z are as defined above in the Summary of the Invention. In general the compounds of formula (Ib) are prepared by the hydrolysis of corresponding esters of formula (Ia). In particular, a compound of formula (Ia) is treated with an excess of an inorganic acid, preferably sulfuric acid, in a neutral solvent, preferably tetrahydrofuran, at temperatures between 20° C. and 100° C., for about 20 to 70 hours, preferably for about 40 hoursCompounds of formula (Ib) are then isolated from the reaction mixture by standard isolation techniques, preferably by cooling and filtration. Alternatively, a compound of formula (Ia) is treated with an excess of base, preferably an alkaline metal hydroxide, for example, lithium hydroxide, in a protic solvent, preferably aqueous methanol, at temperatures between −40° C. and −10° C., preferably between −30° C. to −15° C. The hydrolysis is then quenched by the addition of an inorganic acid, preferably hydrochloric acid, and by the slow addition of water. The resulting mixture is then stirred for about 30 minutes to about 2 hours, preferably for 1 hour, at temperatures between 0° C. and 10° C. Compounds of formula (Ib) are then isolated from the reaction mixture by standard isolation techniques, preferably by filtration.

C. Preparation of Compounds of Formula (Ic)

The compounds of formula (Ic) are compounds of formula (I) wherein $R^1$, $R^2$, $R^3$ and Z are as defined in the Summary of the Invention above except that $R^4$ is not hydrogen.

Compounds of formula (Ia) are also compounds of formula (Ic). Therefore, compounds of formula (Ia), where $R^1$ is $-OR^4$ (where $R^4$ is lower alkyl) may also be prepared according to the following procedures.

Certain compounds of formula (Ic) wherein $R^1$ is $-OR^4$ (where $R^4$ is lower alkyl, phenyl, phenyl-lower-alkyl, or $-(CH_2)_nY$ where n is an integer from 1 to 4 and Y is morpholino, $-C(O)N(R^6)_2$, or $-N(R^6)_2$, in which each $R^6$ is independently selected from hydrogen or lower alkyl) or $-SR^7$ (where $R^7$ is lower alkyl, phenyl-lower-alkyl or $-(CH_2)_nW$ where W is $-N(R^6)_2$, and n and $R^6$ are as previously defined); $R^2$ is lower alkyl, phenyl or phenyl-lower-alkyl; $R^3$ is halo, hydroxy, lower alkyl, $-C(O)OR^5$ where $R^5$ is lower alkyl; and Z is a bond, 2,5-thienyl or 2,5-furanyl, are prepared by esterifying a compound of formula (Ib) with a compound of the formula $R^4OH$ or $R^7SH$ where $R^4$ and $R^7$ are as defined above. In particular, a solution of a compound of formula (Ib) and at least an equimolar amount of an alcohol of formula $R^4OH$ in a neutral solvent, preferably chloroform, is treated with at least an equimolar amount of a tertiary amine, preferably pyridine, cooled to 0° C. and then treated with an inorganic acid halide, preferably phosphorus oxychloride, at temperatures between $-10°$ C. and 10° C., preferably at 0° C., for 30 minutes to 2 hours, preferably for 1 hour. The reaction mixture is then poured into a cold solution of an aprotic solvent, preferably methylene chloride, and an excess of an inorganic acid, preferably hydrochloric acid, to form compounds of formula (Ic), which are isolated from the reaction mixture by standard isolation techniques, preferably by chromatography. Compounds of formula (Ic) wherein $R^1$ is $-OR^4$ where $R^4$ is lower alkyl may also be prepared by the conventional esterification of the corresponding compound of formula (Ib).

Certain comPounds of formula (Ic), wherein $R^1$ is $-OR^4$ (where $R^4$ is hydroxyalkyl or lower alkyl) are prepared by reacting compounds of formula (Ia) with compounds of $R^4OH$ wherein $R^4$ is hydroxyalkyl or lower alkyl. In particular, a mixture of a compound of formula (Ia) and at least an equimolar amount of a compound of formula $R^4$ OH, to which a small amount of a sulfonic acid, preferably p-toluenesulfonic acid, is added, is stirred below reflux temperatures from 16 hours to 72 hours. Compounds of formula (Ic) are then isolated from the reaction mixture by standard isolation techniques.

Certain compounds of formula (Ic), wherein $R^1$ is $-OR^4$ (where $R^4$ is $-(CH_2)_nY$ where n is an integer from 1 to 4 and Y is $-SR^5$ or $-C(O)OR^5$ where $R^5$ is lower alkyl) are prepared by reacting compounds of formula (Ib) with an alkylating agent of the formula $XR^4$ where X is halogen and $R^4$ is as previously defined, for example, ethyl bromoacetate or chloromethyl methyl sulfide, in the presence of a base, for example, tetraalkylammonium hydroxide, preferably tetramethylammonium hydroxide, in an aprotic solvent, preferably dimethylformamide, at room temperature to form compounds of formula (Ic).

Certain compounds of formula (Ic), wherein $R^1$ is $-OR^4$ (where $R^4$ is $-(CH_2)_nY$ where n is an integer from 1 to 4 and Y is $-N^+(R^6)_3X^-$ where each $R^6$ is independently selected frOm hydrOgen or lower alkyl, and X is halogen) or $-OSR^7$ (where $R^7$ is $-(CH_2)_nW$ where W is $-N^+(R^6)_3X^-$, and n, X and $R^6$ are as previously defined), which are choline esters, may be prepared by methods analogous to the methods disclosed in European Published Patent Application No. 0 289 262 (Syntex). In particular, these compounds are treated with an alkylating agent of the formula $R^6X$ where X and $R^6$ are as previously defined, in a neutral solvent. preferably diethyl ether, to afford the appropriate choline ester halide.

D. Preparation of Compounds of Formula (B)

Preparation of the compounds of formula (B) wherein Z is 2,5-thienyl or 2,5-furanyl and $R^3$ is as defined above in the Summary of the Invention, are synthesized as shown in the following Reaction Scheme 2:

REACTION SCHEME 2

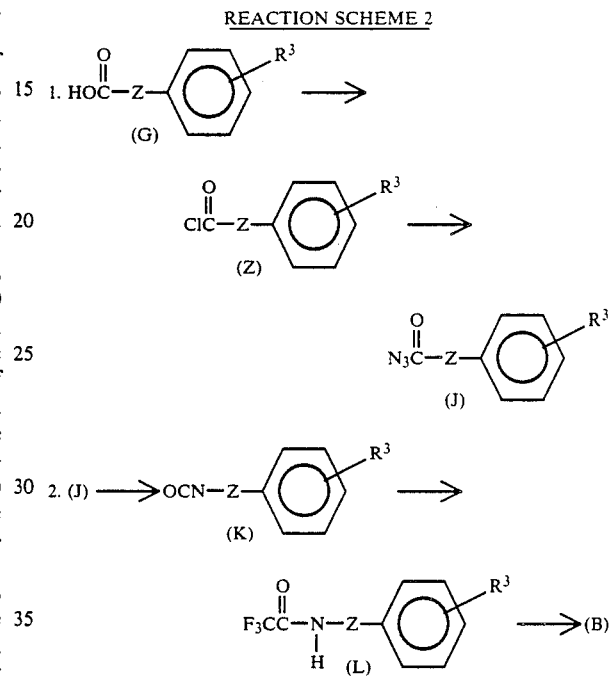

Compounds of formula (G) are prepared according to the method described in European Patent Application 0 259 972.

In general, the compounds of formula (B) are prepared by first adding at least an equimolar amount of an organic acid halide, preferably oxalyl chloride, to a solution of a compound of formula (G) in an aprotic solvent, preferably ethyl a:etate, over a Period of 10 to 15 minutes, preferably over a period of 15 minutes. The reaction mixture is then stirred at room temperature for a 1 to 2 hours, preferably 1½ hours. The solvent is removed to afford compounds of formula (H). Compounds of formula (H) are then dissolved in a neutral solvent, preferably methylene chloride, and then treated with a tetraalkylammonium halide, preferably tetrabutylammonium bromide. An aqueous solution containing an equimolar amount of azide ions is then added to the reaction mixture. The resulting reaction mixture is then stirred at temperatures between $-5°$ C. and 5° C., preferably 0° C., for about 1 to 3 hours, preferably for about 2 hours to form compounds of the formula (J), which are isolated from the reaction mixture by standard isolation techniques, preferably by chromatography and then recrystallization. Compounds of formula (J) are then dissolved in a neutral solvent, preferably toluene, and refluxed for about 30 minutes to 2 hours, preferably for about 1 hour. The solvent is removed to yield compounds of formula (K). Compounds of formula (K) are then dissolved in an aprotic solvent, preferably methylene chloride, and then treated with at least an equimolar amount of a trihaloalkanoic acid, preferably trifluoroacetic acid. The reaction mixture is then stirred for 30 minutes to 2 hours, preferably for 1½ hours, at room temperature and then refluxed for 30 minutes to 2 hours, preferably for 2 hours to afford compounds of formula (L). Compounds of formula (L) are then hydrolyzed under basic conditions to form compounds of formula (B).

In summary, the compounds of formula (I) may be prepared by:

(1) reacting a compound of formula (E) with a compound of formula (F) in a neutral solvent, optionally in the presence of triethylamine, to form a compound of formula (Ia); or (2) hydrolyzing a compound of formula (Ia) to form a compound of formula (Ib); or (3) esterifying a compound of formula (Ib) with an alcohol of the formula $R^4OH$ or a thiol of the formula $R^7SH$ (where $R^4$ and $R^7$ are as defined above in the Summary of the Invention except that $R^4$ is not hydrogen or hydroxyalkyl, Y is not $-SR^5$, $-C(O)OR^5$, or $-N^+(R^6)_3X^-$, and W is not $-N^+(R^6)_3X^-$) to form a compound of formula (Ic); or (4) reacting a compound of formula (Ia) with an alcohol of formula $R^4OH$, where $R^4$ is hydroxyalkyl or lower alkyl in the presence of an acid catalyst to form a compound of formula (Ic) where $R^4$ is hydroxyalkyl or lower alkyl; or (5) reacting a compound of formula (Ib) with an alkylating agent of the formula $X(CH_2)_nY$ where X is halogen and Y is $-SR^5$ or $-C(O)OR^5$ to form a compound of formula (I:) where Y is $-SR^5$ or $-C(O)OR^5$; or (6) reacting a compound of formula (Ic) wherein Y or W is $-N(R^6)_2$ with an alkylating agent of the formula $R^6X$ where $R^6$ is lower alkyl and X is halogen to form a compound of formula (Ic) wherein Y or W is $-N^+(R^6)_3X^-$.

In addition, all compounds of formula (I) that exist in free a:id form may be converted to their pharmaceutically acceptable salts by treatment with the appropriate inorganic or organic base.

The following preparations and examples are given to enable those skilled in the art to more clearly understand and to practice the instant invention. They should not be considered as a limitation on the scope of the invention, but merely as being illustrative and representative thereof.

PREPARATION 1

(Preparation of Compounds of Formula (C) where Z is a bond, Step 1a of Reaction Scheme 1)

A. Diketene (24.7 mL, 0.324 mol) was added dropwise to a 45° C. solution of trifluoromethylaniline (25.5 g, 0.158 mol) in toluene (250 mL). The reaction mixture was stirred at 55° C. for 4 hours and then cooled room temperature. The precipitated crystals are filtered off, washed with cold toluene and dried to afford 35.31 g (91.1%) of 3-oxo-N-(4'-trifluoromethylphenyl)butanamide, m.p. 144°-145° C.

B. In a similar manner, but replacing trifluoromethylaniline with other appropriately substituted anilines, the following compounds were made:

3-oxo-N-(4'-trifluoromethoxyphenyl)butanamide, m.p. 113°-114° C.;
3-oxo-N-(4'-methoxyphenyl)butanamide;
3-oxo-N-(4'-chlorophenyl)butanamide;
3-oxo-N-(2'-hydroxyphenyl)butanamide;
3-oxo-N-(4'-n-butylphenyl)butanamide; and
3-oxo-N-(4'-ethoxycarbonylphenyl)butanamide.

C. In a similar manner, the following compounds are made:

3-oxo-N-(4'-ethoxyphenyl)butanamide;
3-oxo-N-(4'-difluoromethylphenyl)butanamide;
3-oxo-N-(4'-ethylphenyl)butanamide;
3-oxo-N-(4'-bromophenyl)butanamide;
3-oxo-N-(3',5'-dichlorophenyl)butanamide;
3-oxo-N-(3'-trifluoromethoxyphenyl)butanamide;
3-oxo-N-(3'-trifluoromethylphenyl)butanamide;
3-oxo-N-(3'-chlorophenyl)butanamide;
3-oxo-N-(4'-difluoromethoxyphenyl)butanamide;
3-oxo-N-(4'-(1,1-dimethylethyl)phenyl)butanamide;
3-oxo-N-(4'-ethylphenyl)butanamide; and
3-oxo-N-(4'-bromophenyl)butanamide.

PREPARATION 2

(Preparation of Compounds of Formula (C) where Z is a bond, Step 1b of Reaction Scheme 1)

A. Trifluoromethylaniline (25 g) was added to a solution of 2,2,6-trimethyl-2H,4H-1,3-dioxin-4-one (44 mL) in xylene (90 mL). The reaction mixture was heated in an oil bath at 140° C. and allowed to reflux for 35 minutes wherein the formed acetone was removed by distillation. Ethyl acetate (10 mL) was then added to the reaction mixture. The reaction mixture was then allowed to cool to room temperature. The product was then collected by filtration and chromatographed on silica gel (400 g, elute with methanol/methylene chloride mixtures). The purified product was recrystallized from ethyl acetate to afford 4.288 g of 3-oxo-N-(4'-trifluoromethylphenyl)butanamide, m.p. 144°-145° C.

B. In a similar manner, but replacing 2,2,6-trimethyl-2H,4H-1,3-dioxin-4-one with 2,2-dimethyl-6-phenyl-2H,4H-1,3-dioxin-4-one, the following compound was made:

3-oxo-3-phenyl-N-(4'-trifluoromethyl)phenylpropanamide.

C. In a similar manner, the following compounds are made:

3-oxo-4-phenyl-N-(4'-trifluoromethyl)phenylbutanamide;
3-oxo-N-(4'-trifluoromethylphenyl)pentanamide;
3-oxo-5-phenyl-N-(4'-trifluoromethyl)phenylpentanamide.

PREPARATION 3

(Preparation of Compounds of Formula (E))

A. A mixture of 3-oxo-N-(4'-trifluoromethylphenyl)-butanamide (27.06 g, 0.11 mol), as prepared in Preparation 1 above, and pyrrolidine (11 mL, 0.132 mol) in 250 mL of benzene was refluxed for one hour uSing a Dean-Stark trap to separate water. On cooling to room temperature the precipitate was collected by filtration and washed with cold benzene to yield 29.32 g of N-(4'-trifluoromethyl)phenyl-3-pyrrolidyl-2-butenamide (74%), m.p. 198°-200° C.

B. In a similar manner, but replacing N-(4'-trifluoromethyl)phenyl-3-oxobutanamide with the appropriately substituted 3-oxobutanamide, the following compound were made:

N-(4'-trifluoromethoxy)phenyl-3-pyrrolidyl-2-butenamide, m.p. 130°-131° C.;
N-(4'-methoxy)phenyl-3-pyrrolidyl-2-butenamide;
N-(4'-chloro)phenyl-3-pyrrolidyl-2-butenamide;

N-(4'-ethoxycarbonyl)phenyl-3-pyrrolidyl-2-butenamide;
N-(4'-hydroxy)phenyl-3-pyrrolidyl-2-butenamide; and
N-(4'-n-butyl)phenyl-3-pyrrolidyl-2-butenamide.

C. In a similar manner, but replacing pyrrolidine with other cyclic secondary amines of formula (D), the following compounds are made:
N-(4'-trifluoromethyl)phenyl-3-morpholino-2-butenamide; and
N-(4'-trifluoromethyl)phenyl-3-piperidyl-2-butenamide.

PREPARATION 4

(Preparation of Compounds of Formula (J))

A. To a solution of 2-carboxy-5-(4'-(1,1-dimethylethyl)phenyl)thiophene (11.42 g, 0.0439 mol), which was prepared according to this method described in European Patent Application 0 259 972, in ethyl acetate (125 mL) was added three drops of dimethylformamide and then stirred at room temperature. To this reaction mixture 1.2 equivalents of oxalyl chloride (20 mL) was added over a period of 15 minutes. The reaction mixture was then stirred at room temperature for 1½ hours. The ethyl acetate was then removed under reduced pressure to afford a yellow solid, a compound of formula (H). The yellow solid was dissolved in methylene chloride (70 mL) and the resulting solution was cooled. To this solution tetrabutylammonium bromide (200 mg) was added and then an aqueous solution of sodium azide (4.0 g in 15 mL H$_2$O) was added. The reaction mixture was stirred at 0° C. for 2 hours. The reaction mixture was then washed twice with water (150 mL) and then dried over magnesium sulfate. The product was then purified by chromatography on silica gel (400 g, elute with ethyl acetate/hexane (20/80)) and then recrystallized from t-butyl methyl ether and hexane to yield 3.64 g of 2-azidocarbonyl-5-(4'-(1,1-dimethylethyl)phenyl)thiophene, m.p. 162°–164.5° C.

B. In a similar manner, but replacing 2-carboxy-5-(4'-(1,1-dimethylethyl)phenyl)thiophene with other appropriately substituted acids, the following compounds are made:
2-azidocarbonyl-5-(4'-trifluoromethyl)phenylthiophene;
2-azidocarbonyl-5-(4'-trifluoromethoxy)phenylthiophene;
2-azidocarbonyl-5-(4'-methoxyphenyl)thiophene;
2-azidocarbonyl-5-(3',5'-dichlorophenyl)thiophene;
2-azidocarbonyl-5-(4'-chlorophenyl)thiophene;
2-azidocarbonyl-5-(4'-methylphenyl)thiophene;
2-azidocarbonyl-5-(3',5'-dimethylphenyl)thiophene;
2-azidocarbonyl-5-(4'-difluoromethyl)phenylthiophene;
2-azidocarbonyl-5-(4'-difluoromethoxy)phenylthiophene;
2-azidocarbonyl-5-(3'-methoxyphenyl)thiophene;
2-azidocarbonyl-5-(2'-hydroxyphenyl)thiophene;
2-azidocarbonyl-5-(3'-chlorophenyl)thiophene;
2-azidocarbonyl-5-(5'-methylphenyl)thiophene;
2-azidocarbonyl-5-(3'-chloro-5'-methyl)phenylthiophene; and
2-azidocarbonyl-5-(4'-ethoxycarbonyl)phenylthiophene.

C. In a similar manner, but replacing 2-carboxy-5-(4'-(1,1-dimethylethyl)phenyl)thiophene with 2-carboxy-5-(4'-(1,1-dimethylethyl)phenyl)furan, the following compound is made:
2-azidocarbonyl-5-(4'-(1,1-dimethylethyl)phenyl)furan.

D. In a similar manner, but replacing 2-carboxy-5-(4-(1,1-dimethylethyl)phenyl)furan with other appropriately substituted furans, the following compounds are made:
2-azidocarbonyl-5-(4'-trifluoromethylphenyl)furan;
2-azidocarbonyl-5-(4'-trifluoromethoxyphenyl)furan;
2-azidocarbonyl-5-(4'-methoxyphenyl)furan;
2-azidocarbonyl-5-(3',5'-dichlorophenyl)furan;
2-azidocarbonyl-5-(4'-chlorophenyl)furan; and
2-azidocarbonyl-5-(4'-methylphenyl)furan.

PREPARATION 5

(Preparation of Compounds of Formula (B) where Z is 2,5-thienyl or 2,5-furanyl)

A solution of 3.5 g of 2-azidocarbonyl-5-(4'-(1,1-dimethylethyl)phenyl)thiophene, as prepared in Preparation 4, in toluene (100 mL) was refluxed for one hour. The toluene was then evaporated under reduced pressure to give the isocyanate, a compound of formula (K). The isocyanate was dissolved in methylene chloride (50 mL) and then treated with trifluoroacetic acid (3.0 mL). The reaction mixture was stirred for 1½ hours at room temperature and then refluxed for 2 hours to give the trifluoroacetamide, a compound of formula (L). The solvent was removed under reduced pressure. The resulting residue was then hydrolyzed by refluxing for 3 hours with a mixture of potassium carbonate (3.0 g), water (60 mL) and methanol (15 mL). The reaction mixture was cooled and then extracted with methylene chloride. Evaporation of the extracts gave N-[5-(4'-(1,1-dimethylethyl)phenyl)thien-2-yl]amine.

B. In a similar manner, but replacing 2-azidocarbonyl-5-(4'-(1,1-dimethylethyl)phenyl)thiophene with other appropriately substituted acyl azides, the following compounds are made:
N-[5-(4'-trifluoromethylphenyl)thien-2-yl]amine;
N-[5-(4'-trifluoromethoxyphenyl)thien-2-yl]amine;
N-[5-(4'-methoxyphenyl)thien-2-yl]amine;
N-[5-(3',5'-dichlorophenyl)thien-2-yl]amine;
N-[5-(4'-chlorophenyl)thien-2-yl]amine;
N-[5-(4'-methylphenyl)thien-2-yl]amine;
N-[5-(3',5'-dimethylphenyl)thien 2-yl]amine;
N-[5-(4'-difluoromethylphenyl)thien-2-yl]amine;
N-[5-(4'-difluoromethoxyphenyl)thien 2-yl]amine;
N-[5-(3'-methoxyphenyl)thien-2-yl]amine;
N-[5-(2'-hydroxyphenyl)thien-2-yl]amine;
N-[5-(3'-chlorophenyl)thien-2-yl]amine;
N-[5-(5'-methylphenyl)thien-2-yl]amine;
N-[5-(3'-chloro-5'-methylphenyl)thien-2-yl]amine;
N-[5-(4'-ethoxycarbonylphenyl)thien-2-yl]amine;
N-[5-(4'-(1,1-dimethylethyl)phenyl)furanyl-2-yl]amine;
N-[5-(4'-trifluoromethylphenyl)furanyl-2-yl]amine;
N-[5-(4'-trifluoromethoxyphenyl)furanyl-2-yl]amine;
N-[5-(4'-methoxyphenyl)furanyl-2-yl]amine;
N-[5-(3',5'-dichlorophenyl)furanyl-2-yl]amine;
N-[5-(4'-chlorophenyl)furanyl-2-yl]amine; and
N-[5-(4'-methylphenyl)furanyl-2-yl]amine.

PREPARATION 6

(Preparation of Compounds of Formula (E) where Z is 2,5-thienyl or 2,5-furanyl)

A. N-[5-(4'-(1,1-dimethylethyl)phenyl)thien-2-yl]amine, as prepared in Preparation 5, was dis tetrahydrofuran (50 mL). The solution was then treated with diketene (3.0 mL) at 50° C. for 90 minutes. Evaporation of the solvent and chromatography of the residue on silica gel (100 g, elute with ethyl acetate/hexane mixtures)

yielded the acetoacetamide, a compound of formula (C). The acetoacetamide (1.14 g) was then dissolved in benzene (30 mL). The solution was treated with pyrrolidine (0.90 mL) and then refluxed for 2 hours with a Dean Stark trap. The reaction mixture was then cooled to room temperature and the product isolated by filtration to yield 1.130 g of N-5-(4'-(1,1-dimethylethyl)phenyl)thien-2-yl]-3-pyrrolidyl-2-butenamide, m.p. 205°–207° C. B. In a similar manner, but replacing N-[5-(4'-(1,1-dimethylethyl)phenyl)thien-2-yl]amine with other appropriately substituted amines, the following compounds are made:

N-[5-(4'-trifluoromethylphenyl)thien-2-yl]-3-pyrrolidyl-2-butenamide;
N-[5-(4'-trifluoromethoxyphenyl)thien-2-yl]-3-pyrrolidyl 2-butenamide;
N-[5-(4'-methoxyphenyl)thien-2-yl]-3-pyrrolidyl-2-butenamide;
N-[5-(3',5'-dichlorophenyl)thien-2-yl]-3-pyrrolidyl-2-butenamide;
N-[5-(4'-chlorophenyl)thien-2-yl]-3-pyrrolidyl-2-butenamide;
N-[5-(4'-methylphenyl)thien-2-yl]3-pyrrolidyl-2-butenamide;
N-[5-(3',5'-dimethylphenyl)thien-2-yl]-3-pyrrolidyl-2-butenamide;
N-[5-(4'-difluoromethylphenyl)thien-2-yl]-3-pyrrolidyl-2-butenamide;
N-[5-(4'-difluoromethoxyphenyl)thien-2-yl]-3-pyrrolidyl-2-butenamide;
N-[5-(3'-methoxyphenyl)thien-2-yl]-3-pyrrolidyl-2-butenamide;
N-[5-(2'-hydroxyphenyl)thien-2-yl]-3-pyrrolidyl-2-butenamide;
N-[5-(3'-chlorophenyl)thien-2-yl]-3-pyrrolidyl-2-butenamide;
N-[5-(5'-methylphenyl)thien-2-yl]-3-pyrrolidyl-2-butenamide;
N-[5-(3'-chloro -5'-methylphenyl)thien-2-yl]-3-pyrrolidyl-2-butenamide;
N-[5-(4'-ethoxycarbonylphenyl)thien-2-yl]-3-pyrrolidyl-2-butenamide;
N-[5-(4'-(1,1-dimethylethyl)phenyl)furanyl--yl]-3-pyrrolidyl-2-butenamide;
N-[5-(4'-trifluoromethylphenyl)furanyl-2-yl]-3-pyrrolidyl-2-butenamide;
N-[5-(4'-trifluoromethoxyphenyl)furanyl-2-yl]-3-pyrrolidyl-2-butenamide;
N-[5-(4'-methoxyphenyl)furanyl-2-yl]-3-pyrrolidyl-2-butenamide;
N-[5-(3',5'-dichlororphenyl)furanyl-2-yl]-3-pyrrolidyl-2-butenamide;
N-[5-(4'-chlorophenyl)furanyl-2-yl]-3-pyrrolidyl-2-butenamide; and
N-[5-(4'-methylphenyl)furanyl-2-yl]-3-pyrrolidyl-2-butenamide.

EXAMPLE 1

(Preparation of Compounds of Formula (Ia) where Z is a bond)

A. A slurry of N-(4'-trifluoromethyl)phenyl-3-pyrrolidyl-2-butenamide (11.64 g, 0.039 mol), as prepared in Preparation 3 above, in $CH_2Cl_2$ (100 mL) was cooled in an ice bath and treated with ethyl chlorooximidoacetate (7.55 g, 0.05 mol) in one portion. The reaction mixture was stirred at 0° C. for 3 hours and then poured into water. The aqueous layer was extracted with methylene chloride (200 mL) and the combined organic layers were washed with 5% HCl and saturated aqueous $NaHCO_3$ and then dried over $MgSO_4$. Evaporation of the solvent and recrystallization of the residue from ethanol yielded 10.91 g (78% yield) of 3-ethoxycarbonyl-5-methyl-N-(4'-trifluoromethyl)phenyl-4-isoxazolecarboxamide, m.p. 91°–92° C.

B. In a similar manner, but replacing N-(4'-trifluoromethyl)phenyl-3-pyrrolidyl-2-butenamide with an appropriately substituted butenamide the following compounds were made:

3-ethoxycarbonyl-5-methyl-N-(4'-trifluoromethoxy)phenyl-4-isoxazolecarboxamide, m.p. 62°–64° C.;
3-ethoxycarbonyl-5-methyl-N-(4'-methoxy)phenyl-4-isoxazolecarboxamide, m.p. 92°–93° C.;
3-ethoxycarbonyl-5-methyl-N-(4'-chloro)phenyl-4-isoxazolecarboxamide, m.p. 109°–110° C.;
3-ethoxycarbonyl-5-methyl-N-(2'hydroxy)phenyl-4-isoxazolecarboxamide, m.p. 121°–122° C.; and
3-ethoxycarbonyl-5-methyl-N-(4'-ethoxycarbonyl)phenyl-4-isoxazolecarboxamide, m.p. 144°–146° C.

C. In a similar manner, but replacing N-(4'-trifluoromethyl)phenyl-3-pyrrolidyl-2-butenamide with an appropriately substituted 3-phenylpropenamide, the following compounds were made:

3-ethoxycarbonyl-5-phenyl-N-(4'-trifluoromethoxy)phenyl-4-isoxazolecarboxamide, m.p. 96.5°–99° C.;
3-ethoxycarbonyl-5-phenyl-N-(4'-chloro)phenyl-4-isoxazolecarboxamide, m.p. 119°–130° C.;
3-ethoxycarbonyl-5-phenyl-N-(4'-trifluoromethyl)phenyl-4-isoxazolecarboxamide, m.p. 132°–133° C.

D. In a similar manner, but replacing N-(4'-trifluoromethyl)phenyl-3-pyrrolidyl-2-butenamide with an appropriately substituted 3-phenylalkenamide, and ethyl chlorooximidoacetate with the appropriate alkyl chlorooximidoacetate, the following compounds are made:

3-methoxycarbonyl-5-phenyl-N-(4'-methoxy)phenyl-4-isoxazolecarboxamide;
3-methoxycarbonyl-5-phenyl-N-(4'-trifluoromethoxy)phenyl-4-isoxazolecarboxamide;
3-methoxycarbonyl-5-phenylmethyl-N-(4'-methoxy)phenyl-4-isoxazolecarboxamide;
3-methoxycarbonyl-5-phenylmethyl-N-(4'-trifluoromethoxy)phenyl-4-isoxazolecarboxamide;
3-methoxycarbonyl-5-phenyl-N-(4'-chloro)phenyl-4 4-isoxazolecarboxamide; and
3-methoxycarbonyl-5-phenyl-N-(4'-trifluoromethyl)phenyl-4-isoxazolecarboxamide.

EXAMPLE 2

(Preparation of Compounds of Formula (Ib))

A. 3-ethoxycarbonyl-5-methyl-N-(4'-trifluoromethyl)phenyl-4-isoxazolecarboxamide (2.0 g, 5.84 mmol), as prepared in Example 2 above, in tetrahydrofuran (35 mL) was treated with a solution of 20 mL of $H_2SO_4$ (conc.) in 40 mL of water. The reaction mixture was heated at 50° C. for 40 hours and then cooled on ice. The precipitate was then filtered and washed with cold tetrahydrofuran:water (1:2)and then with water. The precipitate was then dried under reduced pressure to yield 1.493 g of 3-carboxy-5-methyl-N-(4'-trifluoromethyl)phenyl-4-isoxazolecarboxamide as a monohydrate (77%), m.p. 226°–227° C.

B. In a similar manner, but replacing 3-ethoxycarbonyl-5-methyl-N-(4'-trifluoromethyl)phenyl-4-isoxazolecarboxamide with an appropriately substituted isoxazolecarboxamide ester, the following compounds were made:

3-carboxy-5-methyl-N-(4'-trifluoromethoxy)phenyl-4-isoxazolecarboxamide, m.p. 144°-146° C.; and 3-carboxy-5-methyl-N-(4'-methoxy)phenyl-4-isoxazolecarboxamide, m.p. 145°-146° C.

C. In a similar manner, the following compounds are made:

3-carboxy-5-methyl-N-(4'-chloro)phenyl-4-isoxazolecarboxamide;

3-carboxy-5-phenyl-N-(4'-trifluoromethoxy)phenyl-4-isoxazolecarboxamide; and 3-carboxy-5-phenyl-N-(4'-methoxy)phenyl-4-isoxazolecarboxamide.

D. Alternatively, a solution of lithium hydroxide (1.07g, 26 mmol) in water (8.0 mL) was diluted with methanol (50 mL) and cooled to $-30°$ C. To this solution was added dropwise a solution of 3-ethoxycarbonyl-5-methyl-N-(4'-trifluoromethyl)phenyl-4-isoxazolecarboxamide (6.84g, 20 mmol) in methanol (85 mL) over a 35 minute period while the reaction temperature was maintained at $-30°$ C. The temperature of the reaction mixture was allowed to rise to $-15°$ C. over a of concentrated HCl (4 mL in 10 mL of water) and the reaction mixture was then diluted by slow addition of 150 mL of water. After stirring the resulting mixture for 1 hour at 0° C. the product was filtered and washed with cold water to yield 6.091 g (19.4 mmol) of 3-carboxy-5-methyl-N-(4'-trifluoromethyl)phenyl-4-isoxazolecarboxamide.

EXAMPLE 3

(Preparation of Compounds of Formula (Ic))

A. A solution of 3-carboxy-5-methyl-N-(4'-trifluoromethyl)phenyl-4-isoxazolecarboxamide (2.0 g, 6.37 mmol), as prepared in Example 2 above, in CHCl$_3$ (8.0 mL) and 1,1-dimethylethanol (t-butyl alcohol) (4.0 mL) was cooled to 0° C. and treated with pyridine (3.0 mL). To this mixture phosphorus oxychloride (0.73 mL, 8.0 mmol) was added dropwise over 5 minutes. After stirring 1 hour at 0° C. the reaction mixture was poured into methylene chloride, ice and 10% aqueous hydrochloric acid. The organic layer was then separated, dried with magnesium sulfate and evaporated in vacuo to give an oily residue, which was purified by silica gel chromatography (250 g, elute with ethyl acetate/hexane (15:85)). The purified residue was recrystallized from t-butyl methyl ether and hexane to yield 1.548 g (66%) of 3-(1,1-dimethylethoxy)carbonyl-5-methyl-N-(4'-trifluoromethyl)phenyl-4-isoxazolecarboxamide, m.p. 133°-134° C.

B. In a similar manner, but replacing 1,1-dimethylethanol with 1-phenylethanol, the following compound was made:

3-(1-phenylethoxy)carbonyl-5-methyl-N-(4'-trifluoromethyl)phenyl-4-isoxazolecarboxamide, m.p. 85°-87° C.

C. In a similar manner, but replacing 1,1-dimethylethanol with ethanethiol, the following compound was made:

3-(ethylthio)carbonyl-5-methyl-N-(4'-trifluoromethyl)phenyl-4-isoxazolecarboxamide, m.p. 92°-93° C.

D. In a similar manner, but replacing 1,1-dimethylethanol with 1,1-dimethylethanethiol and replacing 3-carboxy-5-methyl-N-(4'-trifluoromsthyl)phenyl-4-isoxazolecarboxamide with 3-carboxy-5-methyl-N-(4'-trifluoromethoxy)phenyl-4-isoxazolecarboxamide, the following compound was made:

3-(1,1-dimethylethylthio)carbonyl-5-methyl-N-(4'-trifluoromethoxy)phenyl-4-isoxazolecarboxamide, m.p. 80°-81.5° C.

E. In a similar manner, but replacing 1,1-dimethylethanol with the appropriately substituted alcohol or thiol and 3-carboxy-5-methyl-N-(4'-trifluoromethyl)phenyl-4-isoxazolecarboxamide with the appropriately substituted isoxazolecarboxamide, the following compounds are made:

3-(methoxy)carbonyl-5-methyl-N-(4'-trifluoromethyl)phenyl-4-isoxazolecarboxamide;

3-(ethoxy)carbonyl-5-methyl-N-(4'-trifluoromethyl)phenyl-4-isoxazolecarboxamide;

3-(propoxy)carbonyl-5-methyl-N-(4'-trifluoromethyl)phenyl-4-isoxazolecarboxamide;

3-(phenoxy)carbonyl-5-methyl-N-(4'-trifluoromethyl)phenyl-4-isoxazolecarboxamide;

3-(phenylmethoxy)carbonyl-5-methyl-N-(4'-trifluoromethyl)phenyl-4-isoxazolecarboxamide;

3-(butoxy)carbonyl-5-methyl-N-(4'-trifluoromethyl)phenyl-4-isoxazolecarboxamide;

3-(methylthio)carbonyl-5-methyl-N-(4'-trifluoromethyl)phenyl-4-isoxazolecarboxamide;

3-(propylthio)carbonyl-5-methyl-N-(4'-trifluoromethyl)phenyl-4 isoxazolecarboxamide;

3-(phenylthio)carbonyl-5-methyl-N-(4'-trifluoromethyl)phenyl-4-isoxazolecarboxamide;

3-(phenylmethylthio)carbonyl-5-methyl-N-(4'-trifluoromethyl)phenyl-4-isoxazolecarboxamide;

3-(butylthio)carbonyl-5-methyl-N-(4'-trifluoromethyl)phenyl-4-isoxazolecarboxamide;

3-(methoxy)carbonyl-5-methyl-N-(4'-trifluoromethoxy)phenyl-4-isoxazolecarboxamide;

3-(ethoxy)carbonyl-5-methyl-N-(4'-trifluoromethoxy)phenyl-4-isoxazolecarboxamide;

3-(propoxy)carbonyl-5-methyl-N-(4'-trifluoromethoxy)phenyl-4-isoxazolecarboxamide;

3-(phenoxy)carbonyl-5-methyl-N-(4'-trifluoromethoxy)phenyl-4-isoxazolecarboxamide;

3-(phenylmethoxy)carbonyl-5-methyl-N-(4'-trifluoromethoxy)phenyl-4-isoxazolecarboxamide;

3-(butoxy)carbonyl-5-methyl-N-(4'-trifluoromethoxy)phenyl-4-isoxazolecarboxamide;

3-(methylthio)carbonyl-5-methyl-N-(4'-trifluoromethoxy)phenyl-4-isoxazolecarboxamide;

3-(propylthio)carbonyl-5-methyl-N-(4'-trifluoromethoxy)phenyl-4-isoxazolecarboxamide;

3-(phenylthio)carbonyl-5-methyl-N-(4'-trifluoromethoxy)phenyl-4-isoxazolecarboxamide;

3-(phenylmethylthio)carbonyl-5-methyl-N-(4'-trifluoromethoxy)phenyl-4-isoxazolecarboxamide;

3-(butylthio)carbonyl-5-methyl-N-(4'-trifluoromethoxy)phenyl-4-isoxazolecarboxamide;

3-(2-morpholinoethoxy)carbonyl-5-methyl-N-(4'-trifluoromethyl)phenyl-4-isoxazolecarboxamide;

3-(2-(N',N'-dimethylamino)ethylthio)carbonyl-(5-methyl-N-(4'-trifluoromethyl)phenyl-4-isoxazolecarboxamide;

3-(2-(N',N'-dimethylamino)ethoxy)carbonyl-5-methyl-N-(4'-trifluoromethyl)phenyl-4-isoxazolecarboxamide; and 3-(N',N'-dimethylamino)carbonylmethoxycarbonyl-5-methyl-N-(4'-trifluoromethyl)phenyl-4-isoxazolecarboxamide.

EXAMPLE 4

(Preparation of
3-methoxycarbonyl-5-methyl-N-(4'-trifluoromethyl)-
phenyl-4-isoxazolecarboxamide, a Compound of
Formula (Ic))

3-ethoxycarbonyl-5-methyl-N-(4'-trifluoromethyl)-phenyl-4-isoxazolecarboxamide (2.103 g), as prepared in Example 1 above, was added to methanol (75 mL). The solution was then treated with p-toluenesulfonic acid (50 mg). The reaction mixture was stirred at 52° C. for 72 hours. The resulting reaction mixture was cooled to room temperature and the solvent evaporated under reduced pressure to afford 1.045 g of 3-methoxycarbonyl-5-methyl-N-(4'-trifluoromethyl)phenyl-4-isoxazolecarboxamide, m.p. 130°–131° C.

EXAMPLE 5

(Preparation of
3-(2-hydroxyethoxy)carbonyl-5-methyl-N-(4'-trifluoromethyl)phenyl-4-isoxazolecarboxamide, a
Compound of Formula (Ic))

3-ethoxycarbonyl-5-methyl-N-(4'-trifluoromethyl)-phenyl-4-isoxazolecarboxamide (510 mg), as prepared in Example 1 above, was added to ethylene glycol (8.0 mL) and a few crystals of p-toluenesulfonic acid monohydrate. The solution was stirred at 120° C. overnight and then allowed to cool to room temperature. The reaction mixture was then added to water (50 mL). The resulting reaction mixture was extracted twice with ethyl acetate (50 mL), washed with brine and then dried over magnesium sulfate. The solvent was evaporated under reduced pressure. The resulting product was chromatographed on silica gel (200 g, elute with ethyl acetate/hexane mixtures) and then recrystallized from ethyl acetate/t-butyl methyl ether/hexane to afford 3-(2-hydroxyethoxy)carbonyl-5-methyl-N-(4'-trifluoromethyl)phenyl-4-isoxazolecarboxamide, m.p. 125°–126° C.

EXAMPLE 6

(Preparation of
3-ethoxycarbonylmethoxycarbonyl-5-methyl-N-(4'-trifluoromethyl)phenyl-4-isoxazolecarboxamide, a
Compound of Formula (Ic))

A. Pure tetramethylammonium hydroxide (250 mg) was dispersed in dimethylformamide (15 mL) and cooled to −12° C. in an acetone/ice bath 3-Carboxy-5-methyl-N-(4'-trifluoromethyl)phenyl-4-isoxazolecarboxamide (775 mg, 2.47 mmol), as prepared in Example 2 above, was then added to 5.0 mL of the dimethylformamide solution. After 3 minutes ethyl bromoacetate (4.80 mL) was added and the reaction mixture stirred overnight while being allowed to warm to room temperature. The reaction mixture was then poured into water (400 mL), extracted twice with ethyl acetate (200 mL), washed with brine, and then dried over magnesium sulfate. The solvent was removed under reduced pressure and the residue was then chromatographed on silica gel (100 g, elute with ethyl acetate/hexane mixtures . The product was recrystallized from t-butyl methyl ether and hexane to afford 510 mg of 3-ethoxycarbonylmethoxycarbonyl-5-methyl-N-(4'-trifluoromethyl)phenyl-4-isoxazolecarboxamide, m.p. 110°–111° C.

B. In a similar manner, but replacing ethyl bromoacetate with chloromethyl methyl sulfide, the following compound was made:
3-methylthiomethoxycarbonyl-5-methyl-N-(4'-trifluoromethyl)phenyl-4-isoxazolecarboxamide, m.p. 97°–97.5° C.

C. In a similar manner, but replacing ethyl bromoacetate with methyl bromoacetate, the following compounds is made:
3-methoxycarbonylmethoxycarbonyl-5-methyl-N-(4'-trifluoromethyl)phenyl-4-isoxazolecarboxamide.

EXAMPLE 7

(Preparation of Compounds of Formula (Ia) where Z is
2,5-thienyl or 2,5-furanyl)

A. N-[5-(4'-(1,1-dimethylethyl)phenyl)thien-2-yl]-3-pyrrolidyl-2-butenamide (1.130 g), as prepared in Preparation 6 above, was dissolved in methylene chloride (10 mL), cooled to 0° C. and treated with ethyl chlorooximidoacetate (1.0 g). After 1 hour at 0° C. the reaction mixture was poured into water and extracted with methylene chloride. The extracts were then washed with aqueous sodium chloride, then dried over MgSO4 and evaporated in vacuo. The resulting residue was chromatographed on silica gel (elute with ethyl acetate/hexane mixtures) to afford 0.690 g of 3-ethoxycarbonyl-5-methyl-N-[5-(4'-(1,1-dimethylethyl)phenyl)thien-2-yl]-4-isoxazolecarboxamide, m.p. 132.5°–133° C.

B. In a similar manner, but replacing N-[5-(4'-(1,1-dimethylethyl)phenyl)thien-2-yl]-3-pyrrolidyl-2-butenamide with other appropriately substituted butenamides, the following compounds are made:
3-ethoxycarbonyl-5-methyl-N-[5-(4'-trifluoromethylphenyl)thien-2-yl]-4-isoxazolecarboxamide;
3-ethoxycarbonyl-5-methyl-N-[5-(4'-trifluoromethoxyphenyl)thien-2-yl]-4-isoxazolecarboxamide;
3-ethoxycarbonyl-5-methyl-N-[5-(4'-methoxyphenyl)-thien-2-yl]-4-isoxazolecarboxamide;
3-ethoxycarbonyl-5-methyl-N-[5-(3',5'-dichlorophenyl)thien-2-yl]-4-isoxazolecarboxamide;
3-ethoxycarbonyl-5-methyl-N-[5-(4'-chlorophenyl)thien-2-yl]-4-isoxazolecarboxamide;
3-ethoxycarbonyl-5-methyl-N-[5-(4'-methylphenyl)thien-2-yl]-4-isoxazolecarboxamide;
3-ethoxycarbonyl-5-methyl-N-[5-(3',5'-dimethylphenyl)thien-2-yl]-4-isoxazolecarboxamide;
3-ethoxycarbonyl-5-methyl-N-[5-(4'-difluoromethylphenyl)thien-2-yl]-4-isoxazolecarboxamide;
3-ethoxycarbonyl-5-methyl-N-[5-(4'-difluoromethoxyphenyl)thien-2-yl]-4-isoxazolecarboxamide;
3-ethoxycarbonyl-5-methyl-N-[5-(3'-methoxyphenyl)-thien-2-yl]-4-isoxazolecarboxamide;
3-ethoxycarbonyl-5-methyl-N-[5-(2'-hydroxyphenyl)-thien-2-yl]-4-isoxazolecarboxamide;
3-ethoxycarbonyl-5-methyl-N-[5-(3'-trichlorophenyl)-thien-2-yl]-4-isoxazolecarboxamide;
3-ethoxycarbonyl-5-methyl-N-[5-(5'-methylphenyl)thien-2-yl]-4-isoxazolecarboxamide;
3-ethoxycarbonyl-5-methyl-N-[5-(3'-chloro 5'-methylphenyl)thien-2-yl]-4-isoxazolecarboxamide;
3-ethoxycarbonyl-5-methyl-N-[5-(4'-ethoxycarbonylphenyl)thien-2-yl]-4-isoxazolecarboxamide;

EXAMPLE 8

(Preparation of Compounds of Formula (Ib) where Z is 2,5-thienyl or 2,5-furanyl)

A solution of lithium hydroxide was prepared by dissolving 60 mg of lithium hydroxide in 1 mL of water and adding 6 mL of methanol. This lithium hydroxide solution was cooled to −20° C. and a slurry of 3-ethoxycarbonyl-5-methyl-N-[5-(4′-(1,1-dimethylethyl)-phenyl)thien-2-yl]-4-isoxazolecarboxamide (412 mg), as prepared in Example 7 above, in 15 mL of methanol was added. The reaction mixture was then stirred at -10° C. for 2 hours and then acidified to pH 2 by addition of 10% aqueous hydrochloric acid, followed by addition of 5 mL of water. The resulting mixture was stirred for 3 hours at −10° C. The product was then collected by filtration, and then recrystallized from t-butyl methyl ether and hexane to give 304 mg of 3-carboxy-5-methyl-N-(5-(4′-(1,1-dimethylethyl)phenyl)thien-2-yl-4-isoxazolecarboxamide, m.p. 225°–227° C.

EXAMPLE 9

This example illustrates the preparation of a representative pharmaceutical formulation for oral administration containing an active compound of formula (I), e.g., 3-carboxy-5-methyl-N-(4′-trifluoromethyl)phenyl-4-isoxazolecarboxamide.

| Ingredients | Quantity per tablet. mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of formula (I), such as those prepared in accordance with Examples 1-8, can be used as the active compound in the preparation of the orally administrable formulations of this example.

EXAMPLE 10

This example illustrates the preparation of a representative pharmaceutical formulation containing an active compound of formula (I), e.g., 3-carboxy-5-methyl-N-(4′-trifluoromethyl)phenyl-4-isoxazolecarboxamide.

An injectable preparation buffered to a pH of 4 is prepared having the following composition:

| Intredients | |
| --- | --- |
| Active compound | 0.2 g |
| Sodium Acetate Buffer Solution (0.4 M) | 2.0 mL |
| HCl (1 N) | q.s. to pH 4 |
| water (distilled, sterile) | q.s. to 20 mL |

Other compounds of formula (I), such as those prepared in accordance with Examples 1-8, can be used as the active compound in the preparation of the injectable formulations of this example.

EXAMPLE 11

This example illustrates the preparation of a representative pharmaceutical formulation for topical application containing an active compound of formula (I), e g., 3-carboxy-5-methyl-N-(4′-trifluoromethyl)phenyl-4-isoxazolecarboxamide.

| Ingredients | grams |
| --- | --- |
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. to | 100 |

All of the above ingredients, except water, are combined and heated to 60° C. with stirring. A sufficient quantity of water at 60° C. is then added with vigorous stirring to emulsify the ingredients, and water then added q.s. 100 g. Other compounds of formula (I), such as those prepared in accordance with Examples 1-8, can be used as the active compound in the preparation of the topical formulations of this example.

EXAMPLE 12

This example illustrates the preparation of a representative pharmaceutical formulation containing an active compound of formula (I), e.g., 3-carboxy-5-methyl-N-(4′-trifluoromethyl)phenyl-4-isoxazolecarboxamide.

A suppository totalling 2.5 grams is prepared having the following composition:

Active compound 500 mg witepsol H-15* balance (*triglycerides of saturated vegetable fatty acid; a product of Riches Nelson, Inc., New York, N.Y.).

Other compounds of formula (I), such as those prepared in accordance with Examples 1-8, can be used as the active compound in the preparation of the suppository formulations of this example.

EXAMPLE 13

(In vivo Assay for Anti inflammatory and/or Autoimmune Activity)

This procedure is a modification of a procedure initially described by Winter, et al., *Arthritis and Rheumatism* (1966), Vol. 9, p. 394–403.

Treatment groups of twelve female CD rats (Charles River) were injected intradermally in the tail with 0.1 mL of a mineral oil (Sigma) suspension of heat-killed *Mycobacterium butyricum* (10 mg/mL). Daily administration of compounds of the invention was begun on the same day. The compounds were administered orally in an aqueous vehicle (0.5 mL/dose). Animals in a control group received the same volume of vehicle. On day 17 the intensity of the swelling of the four foot pads and tail was determined utilizing a scoring system in which the swelling in the four paws was scored 0–4 for each paw and the tail swelling is scored 0–3, such that the total maximum score is 19. Polyarthritic animals were scored 0 when no inflammatory signs (swelling and redness) were observed in any of the small joints or large joints. Animals were scored 1 when slight inflammation was observed, 2 for moderate edema, 3 for severe edema and 4 when very severe edema was present. The tail was scored 0 when no signs of edema or necrotic tissue were observed, 1 when inocula injection sites and immediate surrounding tissue exhibited slight edema, 2 when approximately 1/4 of the tail was either inflamed or exhibited necrotic tissue, and 3 when over 1/4 of the tail exhibited severe edema only or edema and necrosis. In addition, hind paw weights of each animal were determined and percent inhibition of the adjuvant-induced gain in paw weight was calculated for each dosing group.

The compounds of the invention showed anti-inflammatory activity and/or activity against auto-immune diseases when tested by this method.

EXAMPLE 14

(In vivo Assay for Immunosuppressive Activity)

This procedure is a modification of "The agar plaque technique for recognizing antibody producing cells "a procedure initially described by Jerne, et al. [*Cell-bound Antibodies*, Amos and Kaprowski editors (Wistar Institute Press, Philadelphia, 1963) p. 109].

Treatment groups of six CD 1 female mice (Charles River) were sensitized with $1 \times 10^8$ sheep red blood cells ("SRBC"). Daily administration of compounds of the invention was begun on the same day. The compounds were administered by injecting the mice orally by gavage with compounds contained in 0.1 mL vehicle. Animals in a control group received the same volume of vehicle. Four days after SRBC. inoculation, spleens were dispersed in glass homogenizers. The number of nucleated cells ("WBC") was determined and the spleen cell suspension was mixed with SRBC., guinea pig complement and agar solution at 0.5% concentration. Aliquots of the above mixture (0.1 mL) were dropped on four separate quadrants of a Petri dish and were covered with cover slips. After two hours incubation at 37° C., areas of hemolysis around plaque-forming cells ("PFC") were counted with a dissecting microscope. Total WBC/spleen, PFC/spleen and PFC/$10^6$ WBC. ("PPM") were calculated for each mouse spleen. Arithmetic means of each treatment group were then compared with the vehicle-treated control group.

The compounds of the present invention show immunosuppressive activity when tested by this assay.

EXAMPLE 15

(In vivo Assay for Immunosuppressive Activity)

This procedure is a modification of the assay as described in Brunner, et al., *Immunology* (1968), Vol. 14, p. 181.

Groups of 4 C57Bl/6 (H-$2^b$) female mice were injected intraperitoneally with $3 \times 10^6$ viable P815 mastocytoma cells (H-$2^d$) in 0.1 mL of phosphate buffered saline. Daily administration of the compounds of the invention was begun on the same day. Ten days after the P815 inJections the mice were sacrificed and their spleens removed. Splenocytes were isolated from the surrounding tissue and suspended in an assay medium consisting of MEM - 10X without 1-glutamine or sodium bicarbonate, 10% heat-inactivated fetal bovine serum, 1-glutamine (2.0 mmol), sodium pyruvate (1.0 mmol), MEM non-essential amino acids (0.1 mmol), sodium bicarbonate solution (1 mg/mL), gentamicin solution (0.05 mg/mL) and 2-mercaptoethanol (0.05 mmol). The splenocytes were counted and diluted in assay medium to $16 \times 10^6$ cells per mL and a series of 4 twofold dilutions were made. Three aliquots (0.1 mL) of ea:h dilution was placed into wells of 96 well U-bottom plates. Target P815 mastocytoma cells were prepared as follows: P815 mastocytoma cells were harvested at maximum cell density of $1 \times 10^6$ cells Per mL. Target cells were collected by centrifugation and $7.5 \times 10^6$ cells were incubated at 37° C. for 2 hours in 1.0 mL of the assay medium into which a small amount of 1.0 mCi/mL solution of sodium chromate (0.1 to 0.2 mL) was added. The labelled target cells were then collected and washed twice by centrifugation through fetal bovine serum. The target cells were then resuspended in 2.0 mL of assay medium, counted, and adjusted to a concentration of $10^5$ cells/mL. The target cell suspension (0.1 mL) was then added to each well of the well plates containing the splenocytes. Effector cell to target cell ratios of 160:1, 80:1 and 40:1 were achieved. Additional wells were incubated with 0.1 mL of the assay medium plus target cells to determine spontaneous release of label. The supernatants of all wells were harvested and counted in a gamma counter. The percent specific cytotoxicity was determined by the following equation:

$$\% \text{ cytotoxicity} = 100 \times \left[ \frac{\text{cpm*/sample} - \text{spontaneous release}}{\text{mcm**} - \text{spontaneous release}} \right]$$

*counts per minute
**maximum counts per minute

The compounds of the invention show immunosuppressive activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula (I):

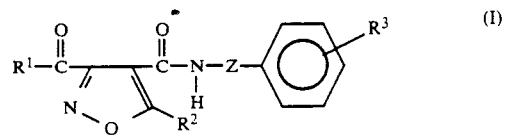

wherein
   $R^1$ is -$OR^4$ (where $R^4$ is hydrogen, lower alkyl, lower hydroxyalkyl, phenyl, phenyl-lower-alkyl, or -$(CH_2)_n Y$ where n is an integer from 1 to 4 and Y is morpholino, -$SR^5$, -$C(O)OR^5$, -$C(O)N(R^6)_2$, -$N(R^6)_2$, or -$N^+(R^6)_3 X^-$, in which $R^5$ is lower alkyl, each $R^6$ is independently selected from hydrogen or lower alkyl, and X is halogen)
   or -$SR^7$ (where $R^7$ is lower alkyl, phenyl-lower-alkyl, or -$(CH_2)_n W$ where W is -$N(R^6)_2$ or -$N^+(R^6)_3 X^-$, and n, $R^6$ and X are as previously defined);
   $R^2$ is lower alkyl, phenyl or phenyl-lower-alkyl;
   $R^3$ is halo, hydroxy, lower alkyl, lower alkoxy lower haloalkyl, lower haloalkoxy, or -$C(O)OR^5$ where $R^5$ is as previously defined; and
   Z is a bond, 2.5-thienyl or 2,5-furanyl; or a pharmaceutically acceptable salt thereof.

2. A compound of claim 1 wherein $R^1$ is -$OR^4$.

3. A compound of claim 2 wherein $R^4$ is hydrogen, lower alkyl or -$(CH_2)_n Y$.

4. A compound of claim 1 wherein $R^2$ is lower alkyl.

5. A compound of claim 4 wherein $R^2$ is methyl.

6. A compound of claim 1 wherein $R^3$ is in the 4'-position and is lower alkyl, lower alkoxy, lower haloalkyl or lower haloalkoxy.

7. A compound of claim 6 wherein $R^3$ is 4'-(1,1-dimethylethyl), 4'-methoxy, 4'-trifluoromethyl or 4'-trifluoromethoxy.

8. A compound of claim 1 wherein Z is a bond.

9. A compound of claim 3 wherein $R^2$ is lower alkyl and Z is a bond.

10. A compound of claim 9 wherein $R^3$ is in the 4'-position and is lower alkyl, lower alkoxy, lower haloalkyl or lower haloalkoxy.

11. A compound of claim 10 wherein $R^1$ is -OH, $R^2$ is methyl, $R^3$ is 4'-trifluoromethyl, namely, 3-carboxy-5-methyl-$\underline{N}$-(4'-trifluoromethyl)phenyl-4-isoxazolecarboxamide.

12. A compound of claim 10 wherein $R^1$ is -OH, $R^2$ is methyl, $R^3$ is 4'-trifluoromethoxy, namely, 3-carboxy-5-methyl-$\underline{N}$-(4'-trifluoromethoxy)phenyl-4-isoxazolecarboxamide.

13. A compound of claim 10 wherein $R^1$ is -OH, $R^2$ is methyl, $R^3$ is 4'-methoxy, namely, 3-carboxy-5-methyl-$\underline{N}$-(4'-methoxy)phenyl-4-isoxazolecarboxamide.

14. A compound of claim 10 wherein $R^1$ is -OH, $R^2$ is methyl, $R^3$ is 4'-(1,1-dimethylethyl), namely, 3-carboxy-5-methyl-$\underline{N}$-(4'-(1,1-dimethylethyl))phenyl-4-isoxazolecarboxamide.

15. A method for treating inflammation in a mammal, wherein the method comprises administering to a mammal in need thereof a therapeutically effective amount of a compound of formula (I):

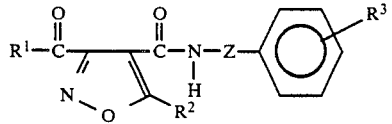

wherein
$R^1$ is -OR$^4$ (where $R^4$ is hydrogen, lower alkyl, lower hydroxyalkyl, phenyl, phenyl-lower-alkyl, or -(CH$_2$)$_n$Y where n is an integer from 1 to 4 and Y is morpholino, -SR$^5$, -C(O)OR$^5$, -C(O)N(R$^6$)$_2$, -N(R$^6$)$_2$, or -N$^+$(R$^6$)$_3$X$^-$, in which $R^5$ is lower alkyl, each $R^6$ is independently selected from hydrogen or lower alkyl, and X is halogen) or -SR$^7$ (where $R^7$ is lower alkyl, phenyl-lower-alkyl, or -(CH$_2$)$_n$W where W is -N(R$^6$)$_2$ or -N$^+$(R$^6$)$_3$X$^-$, and n, $R^6$ and X are as previously defined);

$R^2$ is lower alkyl, phenyl or phenyl-lower-alkyl;

$R^3$ is halo, hydroxy, lower alkyl, lower alkoxy, lower haloalkyl, lower haloalkoxy, or -C(O)OR$^5$ where $R^5$ is as previously defined; and Z is a bond. 2,5-thienyl or 2.5-furanyl; or a pharmaceutically acceptable salt thereof.

16. A composition for treating an autoimmune disease in a mammal which comPosition comprises a pharmaceutically acceptable excipient and a therapeutically effective amount of a compound of formula (I):

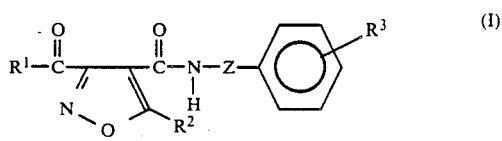

wherein
$R^1$ is -OR$^4$ (where $R^4$ is hydrogen, lower alkyl, lower hydroxyalkyl, phenyl, phenyl-lower-alkyl, or -(CH$_2$)$_n$Y where n is an integer from 1 to 4 and Y is morpholino, -SR$^5$, -C(O)OR$^5$, -C(O)N(R$^6$)$_2$, -N(R$^6$)$_2$, or -N$^+$(R$^6$)$_3$X$^-$, in which $R^5$ is lower alkyl, each $R^6$ is independently selected from hydrogen or lower alkyl, and X is halogen) or -SR$^7$ (where $R^7$ is lower alkyl, phenyl-lower-alkyl, or -(CH$_2$)$_n$W where W is -N(R$^6$)$_2$ or -N$^+$(R$^6$)$_3$X$^-$, and n, $R^6$ and X are as previously defined);

$R^2$ is lower alkyl, phenyl or phenyl-lower-alkyl;

$R^3$ is halo, hydroxy, lower alkyl, lower alkoxy, lower haloalkyl, lower haloalkoxy, or -C(O)OR$^5$ where $R^5$ is as previously defined; and Z is a bond, 2,5-thienyl or 2,5-furanyl; or a pharmaceutically acceptable salt thereof.

* * * * *

UNITED STATES PATENT AND TRADEMARK OFFICE
CERTIFICATE OF CORRECTION

PATENT NO. : 5,001,124

DATED : March 19, 1991

INVENTOR(S) : John W. Patterson

It is certified that error appears in the above-identified patent and that said Letters Patent is hereby corrected as shown below:

On the title page, the "inventors" Section should read:

--[75] Inventor: John W. Patterson, Mountain View, Calif.--

Signed and Sealed this

Twenty-fifth Day of August, 1992

Attest:

DOUGLAS B. COMER

*Attesting Officer*     *Acting Commissioner of Patents and Trademarks*